United States Patent [19]  [11] Patent Number: 4,752,560
Benard et al.  [45] Date of Patent: Jun. 21, 1988

[54] PHOTOGRAPHIC ELEMENT CONTAINING A CYCLIC THIOETHER COMPOUND

[75] Inventors: Rejane R. Benard, La Rochette; Gerard Friour, Chalon-sur-Saone; Marcel L. Riveccie, Rully, all of France

[73] Assignee: Eastman Kodak Company, Rochester, N.Y.

[21] Appl. No.: 905,018

[22] Filed: Sep. 8, 1986

[30] Foreign Application Priority Data

Sep. 24, 1985 [EP] European Pat. Off. ............ 8501850

[51] Int. Cl.$^4$ ................................................ G03C 1/10
[52] U.S. Cl. ..................................... 430/523; 430/603; 430/600; 430/407; 430/564; 430/448; 430/539
[58] Field of Search ............... 430/600, 603, 523, 407, 430/564, 446, 448, 539

[56] References Cited

U.S. PATENT DOCUMENTS

| | | |
|---|---|---|
| 2,521,926 | 9/1950 | Lowe et al. .......................... 430/603 |
| 3,062,646 | 11/1962 | Dann et al. .......................... 430/600 |
| 3,201,242 | 8/1965 | Schwan et al. ...................... 430/469 |
| 3,622,329 | 11/1971 | Huckstadt et al. ................... 430/600 |
| 4,276,374 | 6/1981 | Mifune et al. ....................... 430/603 |

Primary Examiner—Won H. Louie
Attorney, Agent, or Firm—Thomas F. Kirchoff

[57] ABSTRACT

This invention is directed to a photographic element containing a radiation-sensitive silver halide emulsion layer and a cyclic thioether compound comprised of at least one oxygen atom and at least three sulfur atoms, each of said atoms being separated from one another by a divalent alkylene group.

9 Claims, No Drawings

PHOTOGRAPHIC ELEMENT CONTAINING A CYCLIC THIOETHER COMPOUND

This invention relates to a photographic element containing a radiation sensitive silver halide emulsion layer having a thioether compound. More particularly, this invention relates to a photographic element containing a silver halide emulsion and a cyclic thioether compound.

It is known that the addition of certain thioether compounds to various stages of the preparation of silver halide emulsion has the effect of imparting improvements to silver halide properties, such as modification of silver halide crystalline growth or increasing the sensitivity of the resulting crystals.

For example, U.S. Pat. No. 2,521,926, among others, shows that thioether compounds can be used to improve the sensitivity of silver halide emulsions, particularly emulsions sensitized with sulfur and gold compounds. U.S. Pat. No. 3,062,646 describes cyclic thioether compounds which are useful as sensitizers for silver halide. These compounds may comprise two sulfur and two or four oxygen atoms. However, as is shown below by comparative data, these compounds do not provide the level of sensitization that can be obtained with the compounds of this invention.

Various kinds of compounds, incorporated either in a silver halide photographic element or in its developer solution can produce accelerated development. Such compounds are described in C. E. Mees, *The Theory of the Photographic Process*, Macmillan, New York, 4th edition, page 423. Thioethers have been described as development accelerators in U.S. Pat. No. 3,201,242 and in *Research Disclosure*, Vol. 230, June 1983, Item 23005. *Research Disclosure* is published by Kenneth Mason Publications, Ltd., Emsworth, Hampshire P0.010 7DD, England.

However, while particular thioether compounds have effectiveness for increasing the sensitivity of the emulsions or for modifying crystalline growth, production of increased fog is a correlative concern. This risk is inherent in most sensitization operations and is therefore a problem associated with the use of thioether compounds.

Despite the limited successes reported in the art there is an on-going need and search for compounds which improve the sensitivity or crystal modification of silver halide emulsions without objectionably increasing fog.

This invention is directed to a photographic element comprising a radiation sensitive silver halide emulsion layer and a cyclic thioether compound comprised of at least one oxygen atom and at least three divalent sulfur atoms, and wherein adjacent oxygen and sulfur atoms are separated, one from another, by a divalent alkylene group.

Photographic elements containing the described cyclic thioether compounds exhibit improved photographic properties. Specifically, when a cyclic thioether compound as described is incorporated in a silver halide emulsion layer, the speed of the photographic element is increased without experiencing objectionable levels of fog. When a cyclic thioether compound is incorporated in a hydrophilic colloid layer of the photographic element positioned adjacent to the emulsion layer, development acceleration occurs.

The divalent alkylene groups which separate adjacent sulfur and/or oxygen atoms are polymethylene groups. In a preferred embodiment, sulfur and/or oxygen atoms are separated by bridges $-(CH_2)_n-$, wherein n is an integer equal to or higher than 2, most typically 2 or 3.

The described cyclic thioether compounds are particularly effective as co-sensitizers and have an effect which is additive to results obtained from commonly used chemical sensitizing agents, such as sulfur, selenium or gold compounds.

The above described cyclic thioether compounds also permit accelerated development of the photographic elements described herein.

It is believed the effectiveness of the described cyclic thioether compounds is due to an increased solvation action on silver halides, and result from the forming of polynuclear complexes with Ag+ ions. These complexes have the characteristics of being thermodynamically stable and kinetically labile, i.e. they are rapidly dissociated and recomplexed. This property is believed to enhance particularly regulation of sensitization and chemical ripening.

Particular compounds useful in this invention include the following:

Compound 1: 1,4-dioxa-7,10,13-trithiacyclopentadecane:

$CH_2O(CH_2)_2S(CH_2)_2S(CH_2)_2S(CH_2)_2OCH_2$

Compound 2: 1-oxa-6,9,12-trithiacyclohexadecane:

$CH_2S(CH_2)_4O(CH_2)_4S(CH_2)_2SCH_2$

Compound 3: 1,7,13-trioxa-4,10,16-trithiacyclooctadecane:

$CH_2O(CH_2)_2S(CH_2)_2O(CH_2)_2S(CH_2)_2O(CH_2)_2SCH_2$

Compound 4: 1,4,7-trioxa-10,13,16-trithiacyclooctadecane:

$CH_2O(CH_2)_2O(CH_2)_2O(CH_2)_2S(CH_2)_2S(CH_2)_2SCH_2$

Compound 5: 1,4,7,10-tetraoxa-13,16,19-trithiacycloheneicosane:

$CH_2O(CH_2)_2O(CH_2)_2O(CH_2)_2O(CH_2)_2S(CH_2)_2S(CH_2)_2SCH_2$

Compound 6: 1,10-dioxa-4,7,13,16-tetrathiacyclooctadecane:

$CH_2O(CH_2)_2S(CH_2)_2S(CH_2)_2O(CH_2)_2S(CH_2)_2SCH_2$

Cyclic thioether compounds can be prepared by known synthetic processes. In a general manner these compounds are obtained by reacting an α, ω-dihalogenated compound with a dithiol.

One procedure which can be used is described in French Pat. No. 1,377,252, and is as follows:

SYNTHESIS I 3 liters of 50% ethanol are placed in a 4 liter three-necked flask. 10.6 g (0.1 mole) of sodium carbonate $Na_2CO_3$ are added and the mixture is heated to reflux. To the mixture is then added over a 2 hour period a dihalogenated compound (0.1 mole) and a dithiol (0.1 mole). After refluxing for 48 hours, solvents are evaporated in vacuo and the residue is extracted with chloroform. The final product is isolated by chromatography on silica gel (Merck 60H).

A second procedure for preparing cyclic thioether compounds is described by J. Botter, R. M. Kellog, in J. Org. Chem. 1981, page 4481, and is as follows:

SYNTHESIS 2

After flushing with nitrogen, 1250 ml of dimethylformamide (DMF) are placed in a 2 liter three-necked flask. 35.85 g (0.11 mole) of cesium carbonate $Cs_2CO_3$ are then added. The temperature of the reaction medium is raised to 80° C. and a mixture of dihalogenated derivative (0.1 mole) and dithiol (0.1 mole) in solution in 500 ml of DMF is added over an 8 hour period. Upon completion of the addition, the reaction mixture is cooled to room temperature and then filtered. Solvents are evaporated in vacuo and the product is isolated by chromatography on silica gel (Merck 60H).

The following syntheses describe preparations of compounds of this invention.

COMPOUND 1

1,4-dioxa-7,10,13-trithiacyclopentadecane

This compound is obtained by reacting 1,5-dimercapto-3-thiapentane with 1,8-dichloro-3,6-dioxaoctane in the presence of cesium carbonate in dimethylformamide (DMF):

$$HS(CH_2)_2S(CH_2)_2SH + Cl(CH_2)_2O(CH_2)_2O(CH_2)_2Cl$$

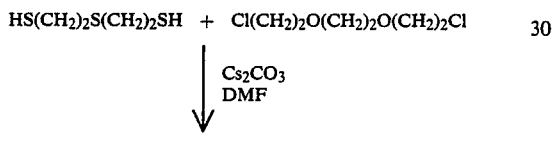

COMPOUND 2

1-oxa-6,9,12-trithiacyclohexadecane

This compound is prepared by first reacting tetrahydrofuran with $POCl_3$ to yield 1,9-dichloro-5-oxanonane:

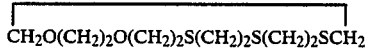

and then reacting the halogenated oxanonane compound with 1,5-dimercapto-3-thiapentane in dimethylformamide in the presence of cesium carbonate:

$$Cl(CH_2)_4O(CH_2)_4Cl + HS(CH_2)_2S(CH_2)_2SH \xrightarrow{Cs_2CO_3}{DMF}$$

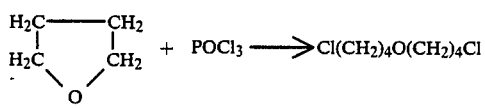

COMPOUND 3

1,7-13-trioxa-4,10,16-trithiacyclooctadecane

The reaction between sodium sulfide and two moles of 2-(2'-chloroethoxy)ethanol yields the intermediate compound 1,11-dihydroxy-3,9-dioxa-6-thiaundecane;

$$Cl(CH_2)_2O(CH_2)_2OH + Na_2S \quad (2)$$

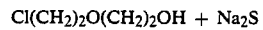

$$HO(CH_2)_2O(CH_2)_2S(CH_2)_2O(CH_2)_2OH$$

Halogenation of the thiaundecane intermediate with thionyl chloride in dimethylsulfoxide (DMF) yields Intermediate A:

$$HO(CH_2)_2O(CH_2)_2S(CH_2)_2O(CH_2)_2OH \quad (A)$$

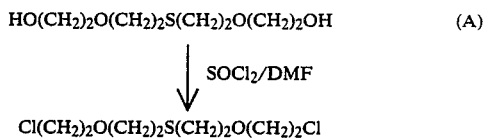

Condensation of Intermediate A with 1,5-dimercapto-3-oxapentane in an aqueous-ethanol solution of sodium carbonate yields Compound 3:

$$Cl(CH_2)_2O(CH_2)_2S(CH_2)_2O(CH_2)_2Cl + HS(CH_2)_2O(CH_2)_2SH$$

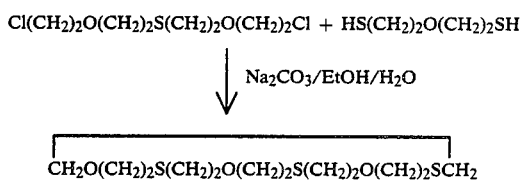

COMPOUND 4

1,4,7-trioxa-10,13,16-trithiacyclooctadecane

This compound is obtained by reacting 1,11-dichloro-3,6,9-trioxaundecane with 1,5-dimercapto-3-thiapentane in the presence of sodium carbonate in aqueous ethanol:

$$HS(CH_2)_2S(CH_2)_2SH + Cl(CH_2)_2O(CH_2)_2O(CH_2)_2O(CH_2)_2Cl$$

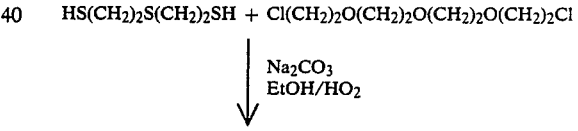

COMPOUND 5

1,4,7,10-tetraoxa-13,16,19-trithiacycloheneicosane

This compound is obtained by reacting 1,5-mercapto-3-thiapentane with 1,14-dichloro-3,6,9,12-tetraoxatetradecane in the presence of sodium carbonate in aqueous ethanol:

$$HS(CH_2)_2S(CH_2)_2SH$$

+

$$Cl(CH_2)_2O(CH_2)_2O(CH_2)_2O(CH_2)_2O(CH_2)_2Cl$$

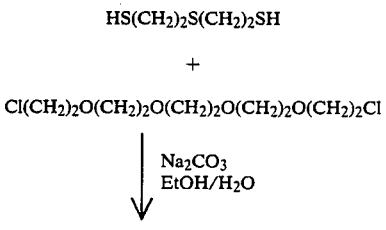

COMPOUND 6

1,10-dioxa-4,7,13,16-tetrathiacyclooctadecane

The reaction between the disodium salt of ethandithiol and two moles of 2-(2'-chloroethoxy)ethanol yields 1,14-dihydroxy-3,12-dioxa-6,9-dithiatetradecane which is then dihalogenated to supply Intermediate B:

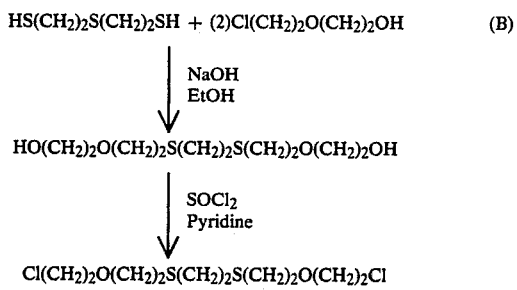

The condensation of B with ethandithiol yields Compound 6.

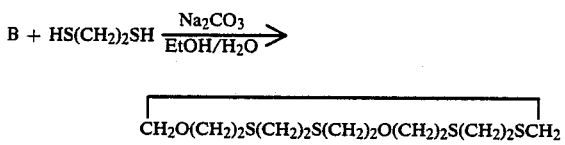

A photographic element of this invention comprises a support and at least one silver halide emulsion layer. The cyclic thioether compound can be present in a silver halide emulsion layer or in another hydrophilic colloid layer, such as an intermediate layer. Since the cyclic thioether compound can function as either or both a co-sensitizing agent and a development accelerating agent in an emulsion layer, it is preferably incorporated in a silver halide emulsion layer. However, when the cyclic thioether is incorporated elsewhere in the photographic element so that it can enter the silver halide emulsion layer during development, such as in an adjacent hydrophilic colloid layer, it can function as a development accelerator.

When it is desired to incorporate a cyclic thioether compound in a silver halide emulsion layer, this can be achieved at any of various steps of the preparation of the emulsion. The preparation of silver halide emulsions is well known and is described, for example, in *Research Disclosure*, Vol. 176, December 1978, Item 17643, paragraphs I and II. The emulsions can be chemically sensitized as described in paragraph III of the same publication. A cyclic thioether compound can be incorporated during a ripening step where it will serve to modify the growth of silver halide grains. The thioether compound can also be incorporated in the chemical sensitization step, preferably simultaneously with other chemical sensitizing agents. Useful amounts of cyclic thioether compound will vary depending upon such factors as the type of emulsion, the particular cyclic thioether selected, and the specific effects that are sought. Generally, amounts range from about $5 \times 10^{-5}$ to about $1 \times 10^{-3}$ mole/silver mole, with from about $1 \times 10^{-4}$ to about $5 \times 10^{-4}$ mole/silver mole being preferred.

Preferably, chemical sensitizing agents employed in combination with cyclic thioethers are sulfur and/or selenium compounds with gold compounds. In comparison to thioether compounds used as co-sensitizing agents according to the prior art, the cyclic thioethers of the present invention provide improved sensitivity to silver halide emulsions without undesirable fog increase. This is shown by examples below.

Alternatively, the cyclic thioether compounds described herein can be incorporated during the melting step for the silver halide emulsion immediately prior to coating. In this case, the amount of thioether compound is preferably from about $1 \times 10^{-4}$ to about $5 \times 10^{-4}$ mole/silver mole.

When a cyclic thioether compound of this invention is incorporated in a hydrophilic colloid layer adjacent to a silver halide emulsion layer, such as in an intermediate layer separating adjacent silver halide emulsion layers, the cyclic thioether is preferably coated at a coverage of from about $1 \times 10^{-7}$ to about $1 \times 10^{-6}$ mg/dm$^2$.

When the thioether compound is incorporated during the melting step prior to coating, or is incorporated in a layer adjacent a silver halide emulsion layer, it is believed that the thioether compound functions primarily as a development accelerating agent rather than as a co-sensitizing agent.

In still another alternative, a cyclic thioether compound of this invention can be incorporated in a photographic element from a processing solution by incorporating the cyclic thioether in the processing solution in an amount of from about $5 \times 10^{-5}$ to about $1 \times 10^{-3}$ mole/liter. In this alternative the thioether compound acts basically as a development accelerator. However, enhancement of the observed speed of the photographic element results regardless of which manner of action is ascribed to the cyclic thioether compound.

The silver halide grains can be of any halide composition (e.g., silver bromide, silver bromoiodide, silver chloride, or silver chlorobromoiodide), of any size (e.g., coarse or fine), and can be of any regular or irregular shape (e.g., spherical, regular cubic, regular octahedral, cubo-octahedral, or tabular octahedral) known to be useful in photography. Conventional vehicles can be used, such as those described in *Research Disclosure* (RD), Item 17643, cited above, paragraph IX. Silver halides can be spectrally sensitized as described in paragraph IV of the same RD reference.

The improvements of this invention can be applied to black and white photography (including radiography) or, preferably, to color photography, to form silver images and/or dye images by selective dye destruction, formation or physical elimination, as described in paragraph VII. Preferred color photographic elements are those that form dye images by means of color developers or dye forming couplers. To use these elements, they can be exposed and processed in any known manner as described in paragraphs XVIII and XIX of the above-mentioned RD reference.

The following examples are presented as further illustrations of the invention.

EXAMPLE 1

A silver bromoiodide gelatin emulsion (1.8% iodide) having nontabular grains of average diameter = 0.75 μm was prepared and thioether compounds, as identified below in Table I, were added thereto from aqueous-methanol solutions. In each instance the thioether concentration was $1.7 \times 10^{-4}$ mole/mole Ag. The resulting mixture was heated to 60° C. and then cooled to 40° C. at which temperature the following sensitizing composition was added:

TABLE II

| | Blue | | | Green | | | Red | | |
| --- | --- | --- | --- | --- | --- | --- | --- | --- | --- |
| *Rel. Speed | Dmin | Dmax | *Rel. Speed | Dmin | Dmax | *Rel. Speed | Dmin | Dmax | |
| 100 | 0.11 | 3.13 | 100 | 0.15 | 3.12 | 100 | 0.09 | 2.73 | |
| 155 | 0.09 | 2.85 | 129 | 0.13 | 2.98 | 145 | 0.07 | 2.57 | |

*Relative Speed measured at 2.20 above Dmin.

| | |
| --- | --- |
| $Na_2S_2O_3$ | 2.9 mg/mole Ag |
| $KAuCl_4$ | 0.6 mg/mole Ag |
| NaSCN | 43.8 mg/mole Ag |

The emulsion was then heated to 65° C. Samples were taken every five minutes, then coated in the presence of glycerol at a coverage of 50 mg silver/dm².

The resulting films were exposed for 1/50th sec. in a sensitometer X6 (2850° K., Wratten 39 filter) and developed for 6 minutes in a hydroquinone/N-methyl-p-aminophenol hemisulfate (Elon ®) developer (Kodak Developer D 19b ®), or for 8 minutes in an Elon ® ascorbic acid (EAA) surface developer.

For comparison purposes the following thioether compound, disclosed in U.S. Pat. No. 3,062,646, was similarly tested:

1,10-dithia-4,7,13,16-tetraoxacyclooctadecane

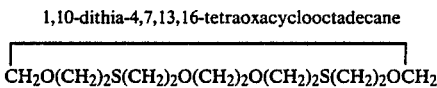

$CH_2O(CH_2)_2S(CH_2)_2O(CH_2)_2O(CH_2)_2S(CH_2)_2OCH_2$

The sensitometric results are shown in Table I.

TABLE I

| Thioether Compound | Developer D 19b ® | | | Developer EAA | |
| --- | --- | --- | --- | --- | --- |
| | Relative Speed | Contrast | Dmin | Relative Speed | Dmin |
| Comparison | 100 | 1.90 | 0.20 | 100 | 0.19 |
| 1 | 159 | 1.80 | 0.25 | 324 | 0.25 |
| 2 | 89 | 1.80 | 0.25 | 490 | 0.30 |
| 3 | 141 | 2.15 | 0.25 | 692 | 0.25 |
| 4 | 159 | 2.30 | 0.25 | 550 | 0.18 |
| 5 | 126 | 2.20 | 0.24 | 955 | 0.30 |
| 6 | 141 | 1.90 | 0.25 | 603 | 0.23 |

These results show that photographic elements having thioether compounds according to this invention exhibit increased speed as compared with the comparison element, whether development is undertaken with Developer D 19b ® or with Developer EAA.

EXAMPLE 2

In a commercial color reversal film (Kodachrome ®), the following amounts of the cyclic thioether 1,4,7-trioxa-10,13,16-trithiacyclooctadecane, which is Compound 4 of this invention, were introduced to the indicated gelatin interlayers:

| | |
| --- | --- |
| UV filter layer | $8 \times 10^{-7}$ mg/dm² |
| Magenta interlayer | $7 \times 10^{-7}$ mg/dm² |
| Cyan interlayer | $1.3 \times 10^{-6}$ mg/dm² |

The film was then exposed and developed in the usual manner. A control film, identical except for the absence of a cyclic thioether compound, was exposed and processed in the same manner.

Table II shows that the speed of the cyclic thioether containing film is markedly increased. The cyclic thioether, as here employed, performs the function of a development accelerator.

Repetition of this example using the prior art cyclic thioether compound, 1,10-dithia-4,7,13,16-tetraoxacyclooctadecane, of U.S. Pat. No. 3,062,646 did not yield any improvement of sensitivity in comparison to the otherwise identical control having no cyclic thioether compound.

This invention has been described in detail with particular reference to preferred embodiments thereof, but it will be understood that variations and modifications can be effected within the spirit and scope of the invention.

What is claimed is:

1. A photographic element comprising a radiation sensitive silver halide emulsion layer and a cyclic thioether compound comprised of at least one oxygen atom and at least three divalent sulfur atoms wherein each of said oxygen and sulfur atoms are separated one from another by a divalent alkylene group, said thioether compound being incorporated in the silver halide emulsion layer, or in a hydrophilic colloid layer adjacent said emulsion layer, to obtain increased speed of said element or to accelerate development thereof.

2. A photographic element according to claim 1 wherein said alkylene group is an ethylene or a propylene group.

3. A photographic element according to claim 2 wherein said thioether compound comprises two oxygen atoms and three sulfur atoms.

4. A photographic element according to claim 3 wherein said thioether compound is chosen from the group consisting of:
1,4-dioxa-7,10,13-trithiacyclopentadecane;
1-oxa-6,9,12-trithiacyclohexadecane;
1,7,13-trioxa-4,10,16-trithiacyclooctadecane;
1,4,7-trioxa-10,13,16-trithiacyclooctadecane;
1,4,7,10-tetraoxa-13,16,19-trithiacycloheneicosane; and
1,10-dioxa-4,7,13,16-tetrathiocyclooctadecane.

5. A photographic element according to claim 1 wherein said thioether compound is located in a silver halide emulsion layer.

6. A photographic element according to claim 5 wherein said thioether compound is present in said emulsion layer in an amount of from about $5 \times 10^{-5}$ to about $1 \times 10^{-3}$ mole/silver mole.

7. A photographic element according to claim 5 wherein said thioether compound is present in said emulsion layer in an amount of from about $1 \times 10^{-4}$ to about $5 \times 10^{-4}$ mole/silver mole.

8. A photographic element according to claim 1 which additionally includes a hydrophilic colloid layer located adjacent to said silver halide emulsion layer and wherein said thioether compound is located within said colloid layer.

9. A photographic element according to claim 8 wherein said thioether compound is present in said colloid layer at a coverage of from about $1 \times 10^{-7}$ to about $1 \times 10^{-6}$ mg/dm².

* * * * *